(12) United States Patent
Massengale et al.

(10) Patent No.: US 10,119,890 B2
(45) Date of Patent: Nov. 6, 2018

(54) WIND DIRECTION-BASED AIR SAMPLING

(71) Applicant: EnRUD Resources, Inc., Pasadena, TX (US)

(72) Inventors: Roy W. Massengale, Webster, TX (US); Wayne T. Boudreaux, Jr., Pasadena, TX (US)

( * ) Notice: Subject to any disclaimer, the term of this patent is extended or adjusted under 35 U.S.C. 154(b) by 51 days.

(21) Appl. No.: 15/017,536

(22) Filed: Feb. 5, 2016

(65) Prior Publication Data

US 2017/0227428 A1    Aug. 10, 2017

(51) Int. Cl.
*G01N 1/20*     (2006.01)
*G01N 1/22*     (2006.01)
*G01N 1/00*     (2006.01)
*G01P 13/02*    (2006.01)

(52) U.S. Cl.
CPC ......... *G01N 1/2214* (2013.01); *G01N 1/2247* (2013.01); *G01P 13/02* (2013.01)

(58) Field of Classification Search
CPC .......... G01N 1/2214; G01N 1/00; G01N 1/22; G01N 1/2202; G01N 1/2217; G01N 1/2247; G01N 1/2273
USPC ............................. 73/863.21, 863.23, 863.01
See application file for complete search history.

(56) References Cited

U.S. PATENT DOCUMENTS 3,420,101 A  * 1/1969  Adams ................. G01P 3/4802
                                                340/870.15
5,297,421 A    3/1994  Hosonuma et al.
5,390,530 A    2/1995  Hosonuma et al.
5,604,299 A    2/1997  Cobb
6,509,566 B1   1/2003  Wamsley et al.
6,865,926 B2   3/2005  O'Brien et al.
6,952,945 B2  10/2005  O'Brien
7,257,987 B2   8/2007  O'Brien et al.
7,288,760 B2  10/2007  Weitz
7,310,047 B2  12/2007  Al-Wehebi
7,359,804 B2   4/2008  Williams et al.
7,606,274 B2  10/2009  Mirov et al.
7,621,171 B2  11/2009  O'Brien
7,743,643 B2   6/2010  Prince
7,756,683 B2   7/2010  Kilgus
7,934,412 B2   5/2011  Prince
8,233,508 B2   7/2012  Mirov et al.

(Continued)

*Primary Examiner* — Daniel S Larkin
*Assistant Examiner* — Anthony W Megna Fuentes

(57) ABSTRACT

Methods, apparatuses, and systems for air sampling and emissions monitoring based on wind direction, including determining concentrations of air toxics, are contemplated. Some embodiments comprise detecting wind flowing in a first direction and a second direction, exposing a sample collection device to air in response to detecting the first direction and preventing exposure of the sample collection device to air in response to the second direction. Some apparatuses comprise a direction detector, an enclosure, and a sample preventer. Some embodiments comprise a purger configured to purge the sample collection device when preventing exposure of the sample collection device to air. In some embodiments, the sample collection device comprises a diffusive sorbent tube. In some embodiments, the diffusive sorbent tube is configured to collect samples of benzene. Some embodiments comprise a wind vane and sensor configured to provide indication of wind direction. Some embodiments comprise a data collector.

20 Claims, 5 Drawing Sheets

(56) References Cited

U.S. PATENT DOCUMENTS

| | | |
|---|---|---|
| 8,294,899 B2 | 10/2012 | Wong |
| 8,347,688 B2 | 1/2013 | O'Brien |
| 8,510,059 B2 | 8/2013 | Prince |
| 8,578,788 B2 | 11/2013 | Ito |
| 8,595,020 B2 | 11/2013 | Marino |
| 8,613,724 B2 | 12/2013 | Lanier, Jr. et al. |
| 8,949,037 B2 | 2/2015 | Prince et al. |
| 9,075,016 B2 | 7/2015 | Groves |
| 2012/0109583 A1 | 5/2012 | Bartlett et al. |
| 2015/0000375 A1 | 1/2015 | Etyemezian et al. |
| 2015/0185194 A1 | 7/2015 | Prince et al. |
| 2016/0011225 A1 | 1/2016 | Holmes |

* cited by examiner

WIND DIRECTION-BASED AIR SAMPLING

FIELD

The embodiments herein are in the field of emissions monitoring. More particularly, the embodiments relate to methods, apparatuses, and systems for both active and passive air sampling and emissions monitoring based on wind direction, including enabling the determination of concentrations of air toxics.

BACKGROUND

The Environmental Protection Agency (EPA) recently proposed rules that require refineries to conduct continuous monitoring of facility boundaries to determine average concentration of a specific air toxic, specifically benzene. One method outlined in the rules, Method 325A, describes the field or implementation process used at or inside a facility property boundary or from fugitive and area emission sources using passive or diffusive tube samplers (PS). The concentration of airborne volatile organic compounds (VOCs) from fugitive-emission or area-emission sources may be determined using this method, in combination with a companion method, Method 325B.

Companion Method 325B describes requirements for sample preparation and analysis. For example, Method 325B describes the laboratory preparation of sampling tubes, shipment and storage of exposed sampling tubes, and analysis of sampling tubes collected using either the passive sampling procedure or an alternative active, or pumped, sampling method. Method 325B further describes the use of thermal desorption and gas chromatography (TD/GC) analysis of VOCs from fugitive-emission and area-emission sources collected onto sorbent tubes using passive sampling, outlined by Method 325A. Methods 325A and 325B are valid for the measurement of benzene.

BRIEF DESCRIPTION OF THE DRAWINGS

Aspects of the embodiments will become apparent upon reading the following detailed description and upon reference to the accompanying drawings in which like references may indicate similar elements.

DETAILED DESCRIPTION OF EMBODIMENTS

Figure 1:
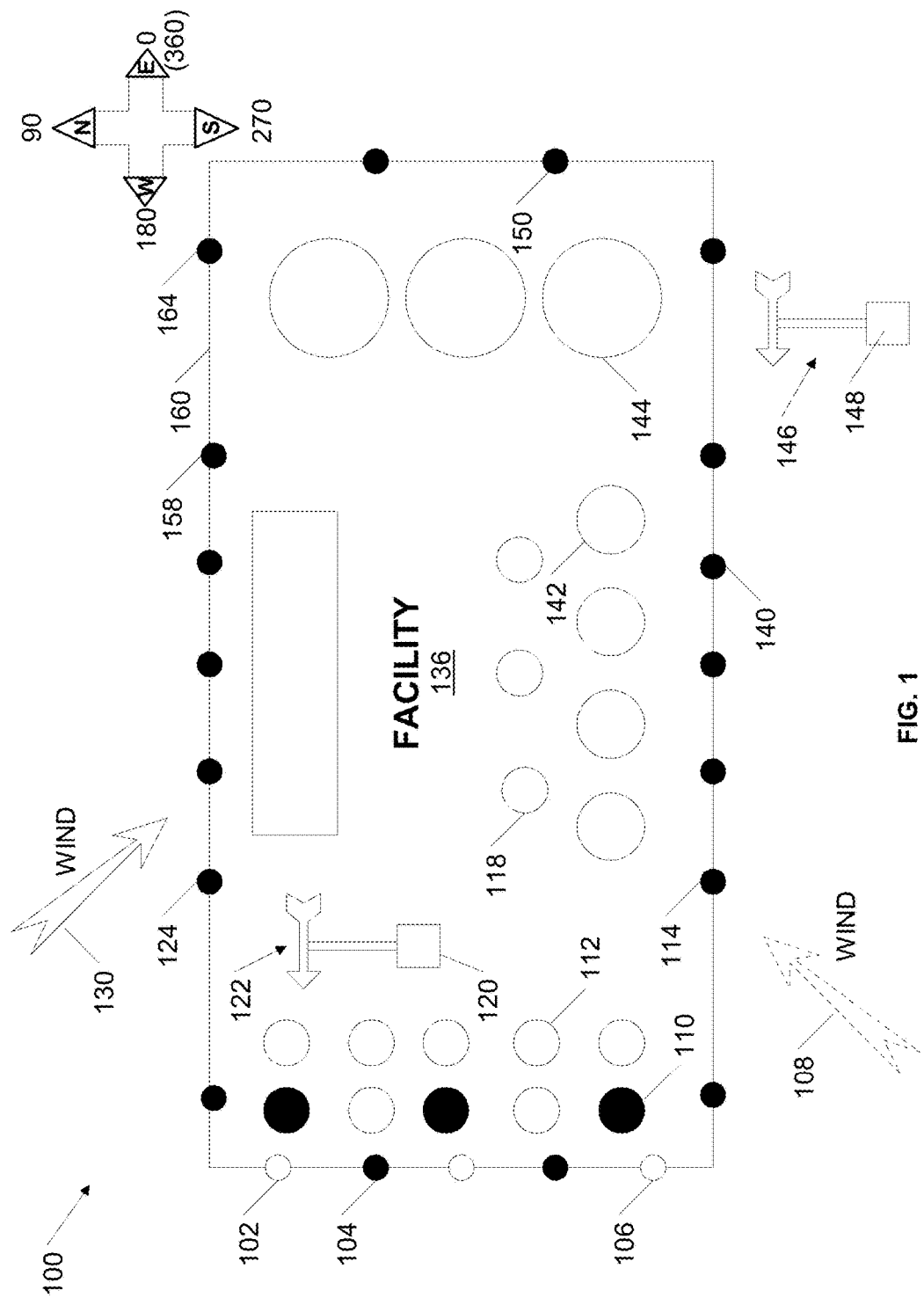
FIG. 1 depicts a facility with multiple sampling stations located along a fence encompassing the facility.

The following is a detailed description of embodiments depicted in the accompanying drawings. The specification is in such detail as to clearly communicate the embodiments. However, the amount of detail offered is not intended to limit the anticipated variations of embodiments; but on the contrary, the intention is to cover all modifications, equivalents, and alternatives consistent with the spirit and scope of the embodiments as defined by the appended claims.

Generally speaking, methods, apparatuses, and systems for air sampling and emissions monitoring based on wind direction, including enabling the determination of concentrations of air toxics, are contemplated. Some embodiments comprise detecting wind flowing in a first and second direction, exposing a sample collection device to air when the wind is flowing in the first direction and preventing exposure of the sample collection device to air when the wind is flowing in the second direction. The embodiments may also comprise purging the sample collection device with nitrogen or purge air in response to detecting the wind flowing in the second direction. In some embodiments, exposing the sample collection device to air may comprise enabling the sample collection device to collect air toxics via adsorption. In other embodiments, exposing the sample collection device to air comprises enabling the sample collection device to collect benzene via adsorption. In other embodiments, enabling the sample collection device to collect benzene may comprise enabling a sorbent to collect benzene via diffusion.

Some embodiments comprise an apparatus for air sampling and emissions monitoring based on wind direction. The apparatus may have numerous elements, such as a direction detector, an enclosure, and a sample preventer. In these embodiments, the direction detector may receive indication of the direction of wind and detect when the wind is flowing in a first direction as well as detect when the wind is flowing in a second direction. The enclosure is configured to retain a sample collection device with a sorbent. The sample preventer is configured to prevent exposure of the sample collection device to air in response to the direction detector detecting the first direction and expose the sample collection device to air in response to the direction detector detecting the second direction.

Some embodiments may also have purger to supply purge gas to the enclosure in response to the direction detector detecting the first direction. Some embodiments may have a cup and a sample collector enclosure. For such embodiments, the preventer is configured to prevent the exposure of the sample collection device to air by coupling the cup to the sample collector enclosure. In some embodiments, the purger may have a purge gas cylinder, a pressure regulator, and a solenoid valve coupled to the sample collector enclosure. For some of these embodiments, the direction detector may be a microcontroller, with the microcontroller also able to operate the solenoid valve. Further of these embodiments may also have a solar panel coupled to a battery, which is coupled to the microcontroller. Some apparatuses may have a wind vane and a sensor coupled to the wind vane, with the sensor being able to provide the indication of the direction of wind. In other apparatuses, the enclosure may retain a second collection device in addition to the first sample collection device, with at least one of the sample collection devices having a diffusive sorbent tube.

Some embodiments comprise a system for air sampling and emissions monitoring based on wind direction. A system may have a wind indicator, a direction detector, and a plurality of sampling stations. The wind indicator can sense a first direction and a second direction of wind. The direction detector can receive indication of the first direction and the second direction of wind from the wind indicator. For the plurality of sampling stations, one or more of the stations may have an enclosure to retain a sample collection device, a preventer to prevent exposure of the sample collection device to air when the direction detector receives indication of the first direction of wind and expose the sample collection device to air in response to the direction detector receiving indication of the second wind direction.

In some systems, a one of the sampling stations may have a second enclosure to retain a second sample collection device. This sampling station may also have a second sample preventer to prevent exposure of the second sample collection device to air in response to the direction detector receiving indication of the second direction of wind and expose the second sample collection device to air in response to the direction detector receiving indication of the first direction of wind. In some of these systems, two or more of the sample collection devices may be diffusive sorbent tubes. Some of these systems may also have one purger apply a first purge gas to the sample collection device in response to the direction detector receiving indication of the first direction of wind. The second purger may apply a second purge gas to the second sample collection device in response to the direction detector receiving indication of the second direction of wind.

Some systems may have one or more computers that enable the sample preventer to prevent the exposure of the sample collection device to air and enable the second sample preventer to prevent the exposure of the second sample collection device to air. Some alternative systems may also have one or more of the sampling stations may have a sorbent tube coupled to a pump.

Although the proposed rules and methods currently apply only to petroleum refineries, the regulatory philosophy and requirements may be extended to other types of facilities, such as chemical manufacturing facilities, in the future. Additionally, the requirements of the continuous passive monitoring methods may also be extended to other types of chemical emissions other than benzene, as will be illustrated.

Turning now to the drawings, FIG. 1 depicts a system 100 having a number of sampling stations situated at various locations along a fence 160 that surrounds a facility 136. In many embodiments the facility 136 may comprise a petroleum refinery. In other embodiments, the facility 136 may comprise a chemical manufacturing plant. In alternative embodiments, the facility 136 may comprise just about any type of business, governmental, or personal entity that may have one or more emission sources needing to be monitored or sampled. The fence 160 may define the property boundary of the facility 136. For example, the fence 160 may comprise a number of fence lines which define the metes and bounds of the property boundaries of the facility 136 and may be any shape or configuration. Further, the fence 160 does not need to be on the property boundary. The fence 160 may be well within the actual property boundaries owned or leased by the facility 136, outside the actual property boundaries, or meander around each. The fence 160 may merely establish a confinement area of the facility 160, for which the system 100 may monitor and sample the emissions.

As illustrated in FIG. 1, the facility 136 may have a number of emission sources of air toxics and/or volatile organic compounds. For example, emission source 110, emission source 118, emission source 142, and emission source 144 may potentially be sources of benzene or another VOC or air toxic. The owners of the facility 136 may wish to monitor the fugitive and area emissions from such sources at the areas surrounding the facility 136 by employing the system 100 of sampling stations. By situating a number of sampling stations around the perimeter or boundary lines of the facility 136, such as along the fence 160, the owners may collect samples of benzene, air toxics, or other VOCs from any of the emissions sources, regardless of which source and regardless of which direction the wind flows.

To illustrate, suppose an emission source 112 starts emitting a small concentration of benzene into the air due to a small leak. Also suppose that the wind at the time of the leak is flowing in a first direction 130, to the southeast. As the wind flows, it may dilute the concentration of benzene in the air and carry the benzene toward the southern boundary of facility 136. Due to the wind flowing in the first direction 130, stations in the path of the plume on the southern boundary of the facility 136 may detect or collect samples of benzene. For example, sampling station 114 and sampling station 140 may collect small concentrations of benzene from the leak of the emission source 112 as the plume travels, from the northwest to the southeast, across the southern boundary of the fence 160.

While the emission source 112 continues to emit small amounts of benzene into the air, suppose the directional flow of wind changes from the first direction 130 to a second direction 108. Due to the wind now flowing in the second direction 108, stations in the path of the new plume direction on the northern boundary of the facility 136 may detect or collect samples of benzene. For example, sampling station 124, sampling station 158, and sampling station 164 may collect small concentrations of benzene as the plume travels, from the southwest to the northeast, across the northern boundary of the fence 160.

Suppose the facility 136 has a neighboring petroleum refinery located to the southwest. Further suppose that the neighboring petroleum refinery located to the southwest of the facility 136 also has a small benzene leak. While the wind is flowing in the second direction 108, the wind may prevent benzene from the leak of the emission source 112 from being collected by any of the sampling stations located along the southern portion of the fence 160, such as the sampling station 114 and the sampling station 140. However, the sampling station 114, the sampling station 140, and other sampling stations along the southern and western boundaries of the fence 160, may nonetheless collect samples of benzene due to the leak from the neighboring petroleum refinery located to the southwest.

To prevent the sampling stations located along the western and southern boundaries of the facility 136 from collecting samples of benzene from the neighboring petroleum refinery, the system 100 may employ a wind indicator 122. In one or more embodiments, the wind indicator 122 may sense or detect wind direction of facility 136 and transmit a signal containing information of the wind direction to one or more sampling stations of the system 100. In some embodiments, the wind indicator 122 may comprise a wind vane. In other embodiments, the wind indicator 122 may comprise a device which uses another means to measure wind direction, such as an ultrasonic wind meter, or a plurality of pitot tubes that may employ measuring pressures to determine wind direction.

Continuing with our example, the wind indicator 122 may determine that the wind is flowing from the second direction 108 and transmit signals to one or more sampling stations, conveying information of the wind direction and enabling specific sampling stations to stop collecting samples. By way of a more specific example, the system 100 may employ a transmitter 120 to communicate to sampling stations 102, 104, 106, 114, and 140 that the wind is flowing from the second direction 108, enabling each of the sampling stations to not collect samples. Further, because the wind is flowing in the second direction 108, the system 100 may also employ the transmitter 120 to communicate to sampling stations 124, 158, 164, and 150 that the wind is flowing across the facility 136 in the second direction 108, enabling each of the sampling stations to collect samples.

While the facility 136 is in operation, the system 100 may use information of wind direction to continually monitor emissions originating from the interior of the facility 136 yet not monitor or at least reduce the sampling of emissions that originate from the exterior of the facility 136. By way of illustration, when the wind is flowing from the first direction 130, the system 100 may cause the sampling stations 124, 158, 164, 102, 104, and 106 to not collect environmental air samples, yet cause sampling stations 114, 140, and 150 to collect environmental air samples. When the wind changes direction from the first direction 130 to the second direction 108, the wind indicator 122 may sense this shift in wind direction and enable the system 100 to alter which sampling stations are collecting environmental air samples. Continuing with the example, when the wind stops flowing from the first direction 130 and switches to the second direction 108, the system 100 may cause sampling stations 124, 158, and 164 to change sampling states and start collecting environmental air samples. Conversely, when the wind stops flowing from the first direction 130 and switches to the second direction 108, the system 100 may also cause the sampling stations 114, and 140 to change sampling states and stop collecting environmental air samples.

One may note that the system 100 may not necessarily change the sampling state of a particular sampling station in response to just any change in wind direction. For example, the system 100 may determine that the wind flow changes from the first direction 130 to the second direction 108, yet prevent the sampling stations 150, 102, 104, and 106 from changing sampling states. In other words, the system 100 may prevent sampling stations 102, 104, and 106 from collecting samples of emissions from the west of facility 136, even though the wind changes direction. The system 100 may also enable sampling station 150 to continue collecting environmental samples, because wind from both the first and second directions (130, 108) may still contain emissions from one of the emission sources of the facility 136.

Different embodiments of the system 100 may be configured in different ways and comprise different elements. One alternative embodiment of the system 100 may comprise a second wind indicator 146 that works in conjunction with the wind indicator 122. For example, the wind indicator 122 may transmit information of wind direction via the transmitter 120 to sampling stations 124, 102, 104, 106, and 140, while the second wind indicator 146 may transfer information of the wind direction to sampling stations 114, 158, 164, and 150 via a transmitter 148. Other alternative embodiments may transfer information of the wind direction to different combinations of sampling stations via the transmitters 120 and 148.

In another alternative embodiment of the system 100, the second wind indicator 146 and the transmitter 148 may serve as a backup to the wind indicator 122 and the transmitter 120. For example, the system 100 may normally employ the wind indicator 122 and the transmitter 120 to control the sampling states of the sampling stations of the facility 136 and only employ the second wind indicator 146 and the transmitter 148 when the wind indicator 122 or the transmitter 120 has a failure. In another alternative embodiment of the system 100, the wind indicator 122, the transmitter 120, the second wind indicator 146, and the transmitter 148 may be located away from the facility 136, such as at a regional weather station.

Different embodiments of the system 100 may use different means to communicate wind direction. In one embodiment of the system 100, the transmitter 120 may communicate information of wind direction to one or more sampling stations via a signal using wires. In some configurations the transmitter 120 may transfer wind direction information via a voltage signal which varies according to the wind direction. For example, the transmitter 120 may transmit a direct current (DC) voltage signal that varies between zero volts DC (VDC) and 10 VDC. The transmitter 120 may transmit 0 VDC when the wind direction is flowing directly to the east, transmit 2.5 VDC when the wind direction is to the north, 5 VDC when the wind direction is to the west, 7.5 V DC when the wind direction is to the south, and 10 VDC when the wind direction is slightly south of direct east. In other configurations, transmitter 120 may transfer wind direction information via a current signal which varies according to the wind direction, such as a 4-20 milliamp (mA) signal, as the wind flows between 0 degrees (east) and 359+ degrees (slightly south of direct east).

As one possessing skill in the are will realize, the voltages and currents described may vary in magnitude and vary based on direction, in different embodiments. For example, the transmitter 120 may transmit 0 VDC when the wind direction is flowing directly to the north, transmit 2.5 VDC when the wind direction is to the east, 5 VDC when the wind direction is to the south, 7.5 V DC when the wind direction is to the west, and 10 VDC when the wind direction is slightly west of direct north.

In even further alternative embodiments, the transmitter 120 may communicate information of wind direction via a digital signal, such as a pulse modulated signal which varies in frequency in response to the direction of the wind or possibly even an Ethernet signal which communicates the direction of the wind via numbers, such as 0 or 360 when the wind is blowing to the east or 90 when the wind is blowing north, as examples. In other alternative embodiments, the transmitter 120 may not employ wires to communicate wind direction to one or more of the sampling stations but instead convey information of wind direction wirelessly, such as by wi-fi or radio signals, as examples.

While the system 100 depicted in FIG. 1 comprises two wind indicators (122, 146), alternative embodiments of system 100 may employ varying numbers of wind indicators.

For example, one embodiment of the system 100 may employ one wind indicator for each individual sampling station. Further, while some embodiments of the system 100 may communicate indications of wind direction directly to one or more of the sampling stations and enable the sampling stations to determine when to collect samples, other alternative embodiments of the system 100 may communicate indications of wind direction to one or more other devices that determine under what conditions specific sampling stations collect samples. For example, in one alternative embodiment of the system 100, the transmitter 120 may communicate indications of wind direction to a computer, wherein the computer determines when the sampling stations 102, 104, 106, and 114 should collect samples and sends signals to those sampling stations which cause the stations to switch sampling states. Similarly, in an alternative embodiment, the transmitter 148 may communicate indications of wind direction to a second computer, wherein the second computer determines under what conditions sampling stations 124, 158, 164, 150, and 140 should collect samples and sends signals to those sampling stations which cause the stations to switch sampling states accordingly.

Even further alternative embodiments of the system 100 may comprise a mixture of sampling determination methods, such as having a computer commanding certain sampling stations to sample under certain wind conditions, yet also comprise other sampling stations which independently determine when to sample in response to directly receiving information of wind direction.

One having skill in the art will appreciate that the number and configuration of sampling stations in a system may vary. For example, while the system 100 depicted in FIG. 1 may comprise 21 sampling stations, alternative embodiments may comprise fewer or more sampling stations, which may be placed in different locations around a different shaped facility and a different size facility.

Figure 2:
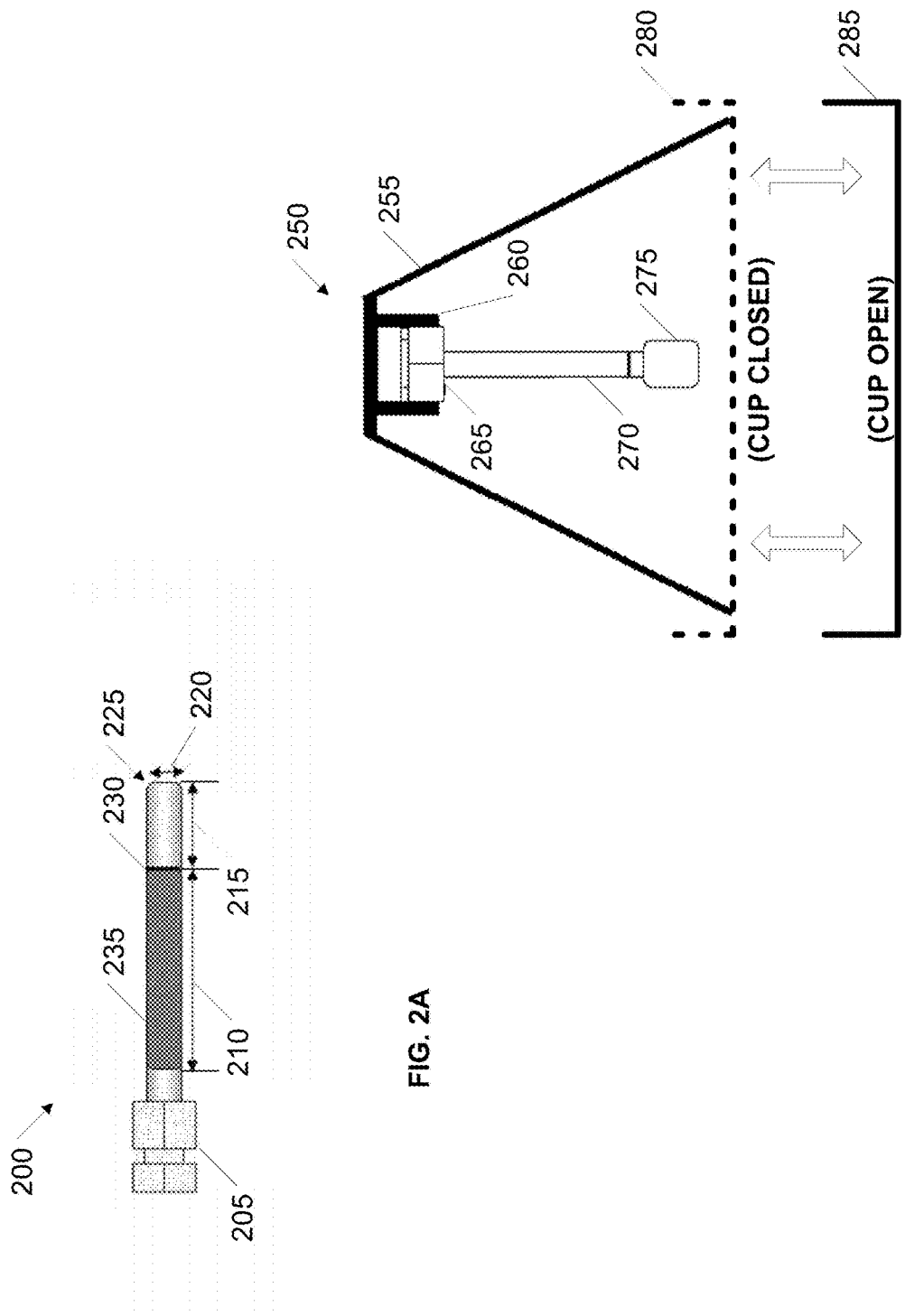
FIG. 2A shows one embodiment of a sample collection device.
FIG. 2B shows one embodiment of an enclosure that may retain one or more sample collection devices.

FIG. 2A depicts a cross-sectional view of an embodiment of a sample collection device 200. The sample collection device 200 may comprise a passive sorbent tube or passive sampler. A passive sampler may refer to a specific type of sorbent tube that has a fixed dimension air gap or diffusion gap 215 at a sampling end 225. In FIG. 2A, the sample collection device 200 comprises a brass cap 205 which may seal the end opposite of the sampling end 225.

The sample collection device 200 may contain a bed length of sorbent 210. For example, various embodiments of the sample collection device 200 may comprise a sorbent 235 having a bed length of up to 60 millimeters (mm) The type of material of the sorbent 235 may vary in different embodiments. In some embodiments, the sorbent 235 may comprise a material which traps one or more analytes of a range of compounds, such as butadiene, benzene, toluene, ethylbenzene, and xylenes, depending on the type of analyte needing to be sampled and measured. In numerous embodiments, the sample collection device 200 may comprise an inert-coated, stainless steel sorbent tube packed with Carbograph™ 1 TD, Carbopack™ B, Carbopack™ X, or other type of sorbent.

Various embodiments may use different terminology when referring to the sample collection device 200. In some embodiments, the sample collection device 200 may be referred to as a sorbent tube. In other embodiments, the sample collection device 200 may be referred to as a tube, a sampling tube, a passive sampler (PS) tube, or an adsorbent tube. In other words, some embodiments may employ a passive collection device, such as a passive sorbent tube, and refer to it using differing terminology. In many embodiments, the sample collection device 200 may have tube dimensions of 3.5-inch (89 mm) long×0.25-inch (6.4 mm) outer diameter (o.d.) with an inner diameter (i.d., element 220) of 5 mm, a cross-sectional area of 19.6 mm2 and an air gap (element 215) of 15 mm. The central portion of the sample collection device 200 may be packed with solid adsorbent material contained between 2×100-mesh stainless steel gauzes and terminated with a diffusion cap (not shown in FIG. 2A) at the sampling end 225. The dimensions, such as those dimensions of the sorbent bed length, the length of the air or diffusion gap 215, the inner diameter 220, cross-sectional area, length, and outer diameter may vary in different embodiments. Additionally, although the embodiment of the sample collection device 200 shown in FIG. 2A comprises a passive sampling tube, alternative embodiments may employ an active sampling device. For example, some alternative embodiments may comprise a sample tube with a sorbent bed coupled to a pump instead of the brass cap 205, wherein the pump draws in air samples from the environment at a fixed or constant rate.

FIG. 2B illustrates how one or more of the sample collection device 200 may be retained by an enclosure 250. For example, one or more of the enclosure 250 may be situated at each sampling station along the fence 160 of the facility 136. In the embodiment depicted in FIG. 2B, the enclosure 250 comprises a weather hood 255 and a tube bracket 260, wherein the tube bracket 260 is configured to retain a diffusive sorbent tube 270 via a brass cap 265. For illustration, the diffusive sorbent tube 270 and the brass cap 265 in FIG. 2B may correspond to the sample collection device 200 with the brass cap 205, respectively, shown in FIG. 2A. The weather hood 255 may be suitable for protecting one or more sample collection devices from harsh weather conditions, such as direct sun, wind, rain, sleet, and snow. The weather hood 255 may comprise an inverted cone or funnel constructed of an inert, non-outgassing material which fits over the diffusive sorbent tube 270, with the open (sampling) end of the diffusive sorbent tube 270 projecting just below the cone opening.

FIG. 2B also illustrates how one or more embodiments may operate to isolate the diffusive sorbent tube 270 and its associated diffusion cap 275 from the environment of a facility. In other words, various embodiments may operate in such a manner as to isolate their respective sample collection devices and prevent the devices from continuing to sample the environment of the facility. As mentioned, the diffusive sorbent tube 270 has the diffusion cap 275. The diffusion cap 275 may fit onto the sampling end of the diffusive sorbent tube 270 during air monitoring.

A portion of the enclosure 250 may comprise a cup. FIG. 2B illustrates how the cup may be positioned sufficiently far away from the sample opening of the weather hood 255, in position 285, enabling the diffusive sorbent tube 270 to collect emission particles which may be in the area or environment immediately surrounding the enclosure 250. For example, when the enclosure 250 is located downwind of a benzene emission source in a facility, various embodiments may detect that the wind is flowing in a direction that could possibly carry the emitted benzene from on-site to off-site and place the cup in the position 285.

The embodiments may continue to monitor the wind direction. If the embodiments detect that the wind changes direction and flows in a different direction that would not carry benzene off-site from the emission source, the embodiments may respond by moving the cup from its open position 285 to a closed position 280. Once the cup has been moved to its closed position 280, the cup may be held firmly against the opening of the weather hood 255 with a gasket in order to seal and isolate the diffusive sorbent tube 270 and the diffusion cap 275 from the facility environment. Stated differently, various embodiments may protect the diffusive sorbent tube 270 from collecting benzene from off-site sources and prevent or reduce the need for complex analyses which would need to correct or adjust the sample for such off-site collection or sampling.

Although the embodiment of the enclosure 250 depicted in FIG. 2B comprises a cone-shaped weather hood 255, alternative embodiments may comprise various other shapes. For example in some embodiments, the weather hood 255 may comprise a cylindrical shaped hood, can, or chamber, having vertical walls instead of cone-shaped walls. Further, the shape of the weather hood 255 may not be circular and instead may be square, rectangular, or other shape, as examples.

While not shown in FIG. 2B, many embodiments may apply a continuous purge to the enclosure 250 and the diffusive sorbent tube 270 whenever the cup is moved to the closed position 280. Activating or applying a purge to the enclosure 250 and the diffusive sorbent tube 270 whenever enclosure 250 is closed and isolated from the environment may help ensure that the diffusive sampling condition of the diffusive sorbent tube 270 is not otherwise disturbed, which may interfere with obtaining a representative and accurate sample of on-site emissions.

Additionally, the embodiment of the enclosure 250 illustrates a single diffusive sorbent tube (element 270). Various embodiments of the enclosure 250 may comprise multiple sample collection devices, including one or more sealed sample collection devices and one or more blanks. For example, one embodiment of the enclosure 250 may retain a total of five tubes, three of which comprise diffusive sorbent tubes having diffusion caps, one tube of which comprises a sealed sorbent tube with no diffusion cap, and a blank tube which comprises no sorbent material.

Figure 3:
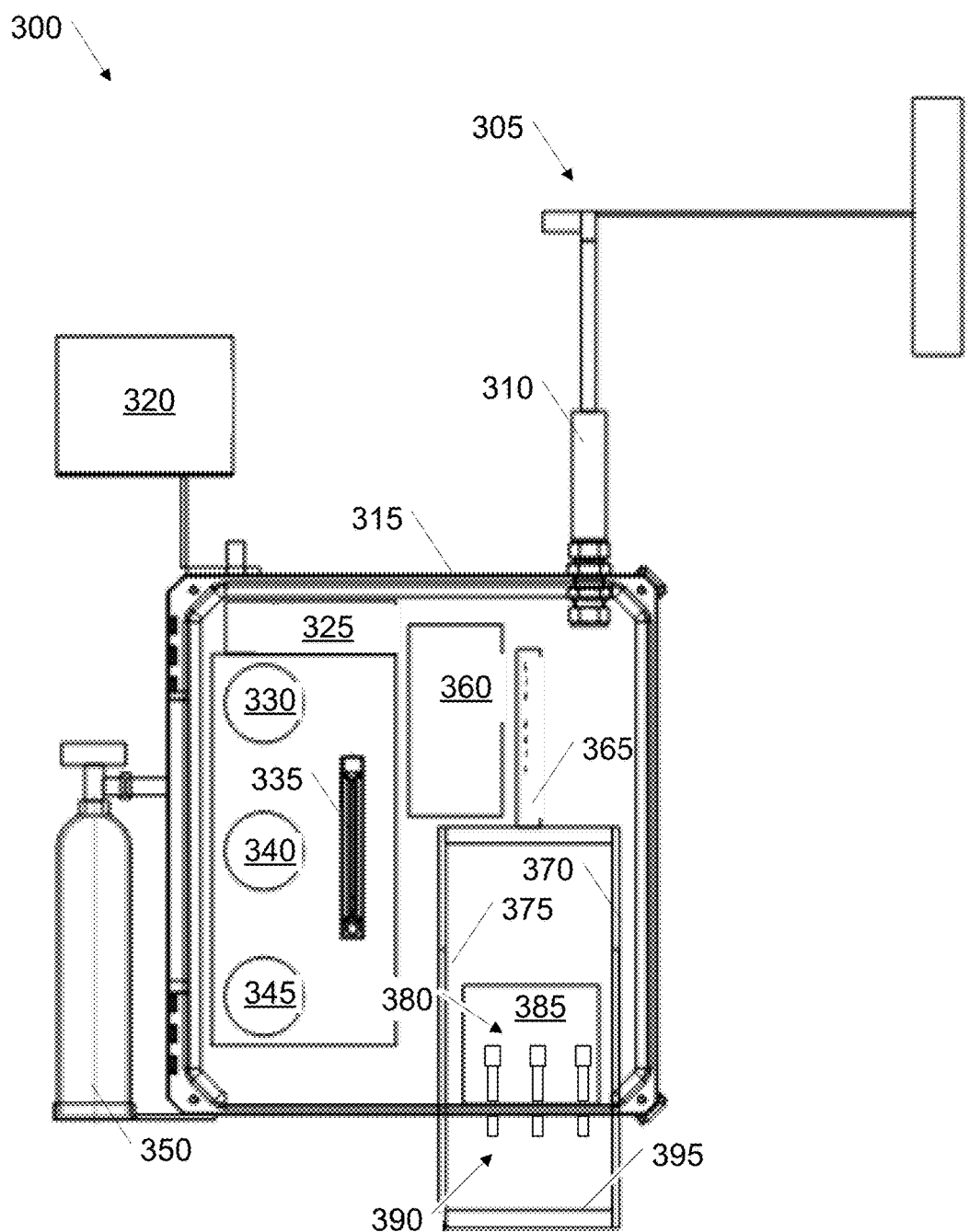
FIG. 3 illustrates a configuration of elements in an apparatus for air sampling in response to wind direction.

FIG. 3 illustrates a configuration of elements of an apparatus 300 for air sampling in response to wind direction. The apparatus 300 comprises a sample collector enclosure 385 which may be configured to retain a plurality of sample collection devices 380. For example, the sample collector enclosure 385 may comprise one embodiment of the weather hood 255 shown in FIG. 2B, wherein the diffusive sorbent tube 270 may comprise one sample collection device of the plurality of sample collection devices 380. Sampling ends 390 of the plurality of sample collection devices 380 may comprise diffusion caps which are open and exposed to the environment when the apparatus 300 is in a state where it is enabling the plurality of sample collection devices 380 to collect samples of air from the environment.

Many of the components of the apparatus 300 may be housed in an overall enclosure 315. Coupled to the outside of the overall enclosure 315, the apparatus 300 comprises a wind vane 305 and a sensor 310 combination that work together to sense or measure the wind direction at the facility location of the apparatus 300. The wind vane 305 may rotate about its vertical axis in response to the flowing direction of the wind. The sensor 310 may sense the position of the wind vane 305 and generate an analog output signal which corresponds to the sensed position. The analog output signal from the sensor 310 may communicate indication of wind direction to a microcontroller 360. The microcontroller 360 may be coupled to a linear actuator 365. The linear actuator 365 may be coupled to a sample isolating lid or sample isolating cup 395. For example, with reference again to FIG. 2B, cup 395 may correspond to the moveable cup of the enclosure 250, which may move between the closed position 280 and the open position 285. In response to the analog output signal that the microcontroller 360 receives from sensor 310, the microcontroller 360 may determine that the plurality of sample collection devices 380 should be isolated to prevent them from collecting further samples of the environment. Upon determining that the plurality of sample collection devices 380 should be isolated from the environment, the microcontroller 360 may activate or trigger the linear actuator 365. In response to the activation from the microcontroller 360, the linear actuator 365 may operate to retract and cause cup 395 to be drawn closer to the sample collection enclosure 385. The linear actuator 365 may move to a fully retracted position whereby arms 375 and 370, which couple the linear actuator 365 with the sample cup 395, may have pulled the sample isolating cup 395 up firmly against the sample collection enclosure 385, isolating the plurality of sample collection devices 380 from being further exposed to the environment and preventing the plurality from collecting additional air samples.

The embodiment of the apparatus 300 depicted in FIG. 3 comprises numerous elements that may operate to apply a purge gas flow to the sample collection enclosure 385 when cup 395 isolates the plurality of sample collection devices 380 from the facility environment. The apparatus 300 comprises a purge gas cylinder 350 mounted to the outside of enclosure 315. Purge gas cylinder 350 may apply a steady flow of purge gas by way of a high pressure gauge 345, a pressure regulator 340, a low pressure gauge 330, and a rotameter 335. For example, the purge gas cylinder 350 may contain an inert gas, such as nitrogen, or uncontaminated air compressed to 3000 pounds per square inch (psi). The high pressure gauge 345 may allow an operator or a technician to estimate the amount of purge gas remaining in the purge gas cylinder 350, as well as establish the proper settings to enable a steady flow of purge gas to the sample collection enclosure 385. The pressure regulator 340 may step down the high pressure of the purge gas cylinder 350 to a lower and much more safe and manageable pressure. For example the pressure regular 340 may decrease the amount of pressure being supplied to low pressure gauge 330 to around 5 psi.

Once the purge gas pressure is reduced via pressure regulator 340, the operator or technician may adjust the rotameter 335 to establish a steady or constant flow rate. In many embodiments the apparatus 300 may also comprise elements to conserve the purge gas. For example, many embodiments may have a solenoid valve situated in the supply line between the discharge of the rotameter 335 and the purge inlet to the sample collection enclosure 385. The microcontroller 360 may conserve the purge gas by either energizing or de-energizing, based on the configuration, the solenoid valve such that the purge gas only flows when the cup 395 is in the closed or isolating position. Whenever the apparatus 300 enables the plurality of sample collection devices 385 to be exposed to the environment and collect samples, the microcontroller 360 may stop the flow of the purge gas by causing the in-line solenoid valve to close. In numerous embodiments, the microcontroller 360 may operate the linear actuator 365 and the solenoid valve simultaneously.

The apparatus 300 in FIG. 3 comprises a battery 325 to supply the power for the operation of the microcontroller 360, the linear actuator 365, and the solenoid valve. To help ensure the battery 325 remains fully charged, the apparatus 300 also comprises a solar panel 320. Alternative embodiments of the apparatus 300 may not employ the battery 325 or the solar panel 320. For example, many embodiments may use 120 Volts AC (VAC) from a local power receptacle located near the apparatus 300. Other alternative embodiments may use both 120 VAC and the battery 325. For example, such alternative embodiments may normally operate using the 120 VAC, which may power a small AC/DC power supply, but fail over to the battery 325 whenever there is a power outage.

The apparatus 300 may be configured to be fail-safe. For example, upon loss of power, or if the microcontroller were to detect some type of operational error, apparatus 300 may cause the cup 395 to move to the fully lowered or extended position, enabling the plurality of sample collection devices to collect air toxics even though the apparatus 300 may have lost power or encountered some other type of error.

Figure 4:
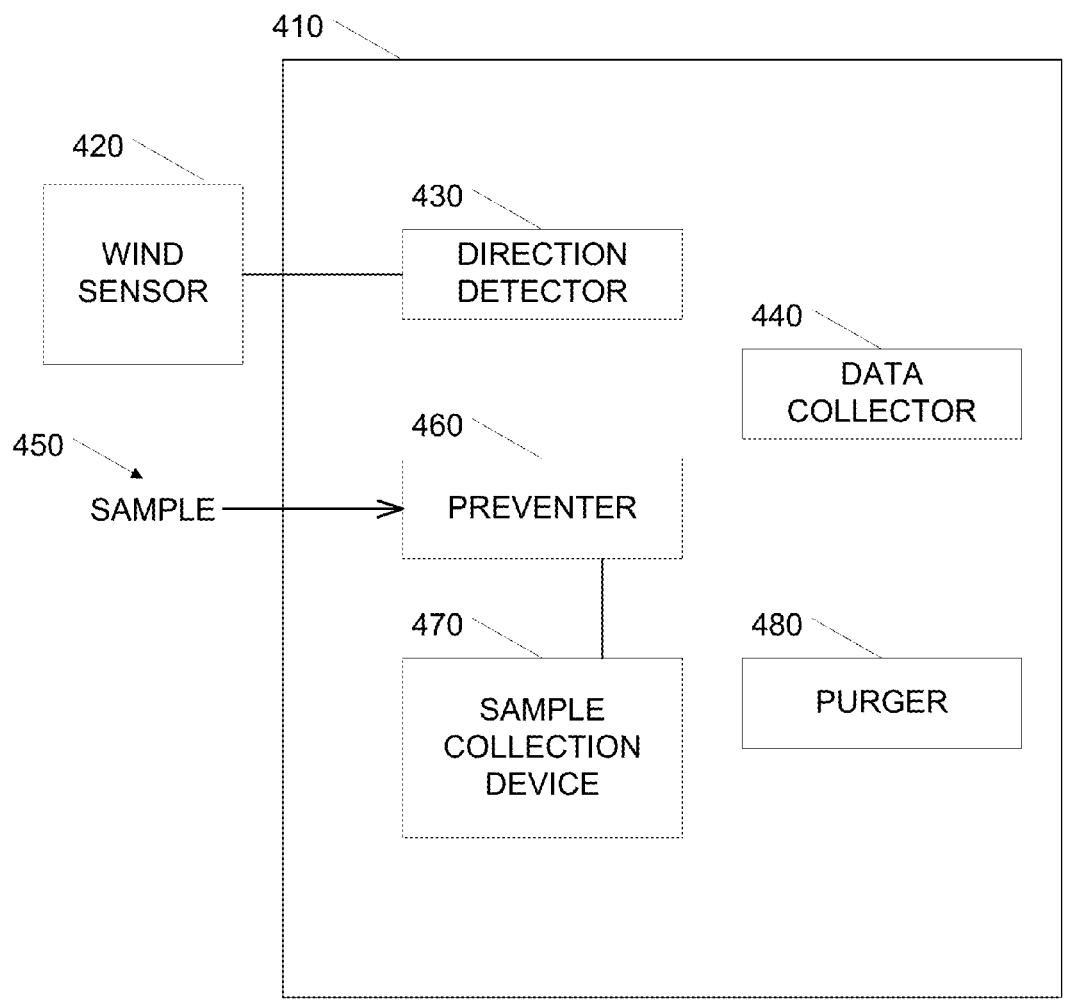
FIG. 4 illustrates an arrangement of elements of an apparatus for air sampling in response to wind direction.

FIG. 4 illustrates an arrangement of elements of an apparatus 410 for air sampling in response to wind direction. With reference to FIG. 1, the apparatus 410 may be one of the sampling stations along the fence 160, such as the sampling station 158 or the sampling station 106, as examples. In other words, one or more of the sampling stations depicted in the system 100 may comprise an apparatus like the apparatus 410. With reference to FIG. 3, the apparatus 410 may be an apparatus having an alternative configuration or arrangement of elements similar to the apparatus 300.

As FIG. 4 depicts, the apparatus 410 comprises a direction detector 430, a preventer 460, and a sample collection device 470. The direction detector 430 may receive a signal or a type of indication of wind direction from a wind sensor, such as wind sensor 420. For example, the wind sensor 420 may comprise a wind vane and accompanying sensor or transmitter, such as the wind vane 305 and the sensor 310 shown in FIG. 3. The wind sensor 420 may sense which direction the wind is blowing and provide indication of the wind direction to the direction detector 430.

In some embodiments, the wind sensor 420 may sense wind direction and provide indication by transmitting an analog signal to the direction detector 430, such as a 1-20 VDC, a 1-5 VDC, a 0-10 VDC, or a 4-20 mA signal which changes in relation to the wind direction. In other embodiments, the wind sensor 420 may sense wind direction and provide indication of the wind direction by transmitting a digital signal to the direction detector 430. Stated differently, the wind sensor 420 may provide indication of wind direction to the direction detector 430 using one or more of a variety of different methods, as will be readily appreciated by one possessing ordinary skill in the art.

As one specific embodiment variation, the wind sensor 420 may provide indication of wind direction via a different means, such as by state or position switches. The embodiment may comprise a wind vane like the wind vane 305 coupled with one or more position switches. In such an embodiment, the position switch may be closed and transmitting a DC or other signal to the direction detector 430 while the wind vane points in one general direction. For example the wind vane may generally be pointing north, indicating the wind is out of the north and blowing in a generally southern direction. The wind vane may vary, such as pointing to the northeast or northwest, but still indicate the wind is generally blowing to the south, wherein the position switch may be configured to remain in the closed position as long as the wind is blowing in the generally southern direction. However, the position switch may be configured to open its contacts when the wind vane passes one or more threshold positions.

Continuing with our example, the position switch may change from closed to open when the wind vane pointer crosses over the east direction, changing from just north of east to just south of east, or opening when the wind vane pointer crosses over the west direction, changing from just north of west to just south of west. In such an embodiment, the direction detector 430 would be arranged to detect when the wind is blowing in the generally southern direction, which would cause the wind vane to point generally north, by monitoring the position switch being closed. The direction detector 430 would detect the wind flow direction changing from a generally southern direction to a generally northern direction by monitoring the position switch changing from the closed position to the open position. As one will appreciate, the number of position switches, as well as the states of the position switches (open vs. closed) may vary in alternative embodiments.

As one having ordinary skill in the art will appreciate, the direction detector 430 may determine wind direction in a variety of different manners in various alternative embodiments. As illustrated, in some embodiments the direction detector 430 may determine wind direction via a 1-5 VDC or a 4-20 mA input signal by comprising an analog-to-digital converter (ADC). In other embodiments, the direction detector 430 may determine wind direction via another means, such as by comprising one or more optoisolators configured to receive digital inputs that change state based on the direction of the wind as sensed and transmitted by the wind sensor 420.

In apparatus 410, the preventer 460 works work in conjunction with the direction detector 430 to either enable the sample collection device 470 to be exposed to a sample 450 or prevent the sample 450 from being exposed to the sample collection device 470. One example of the sample 450 may be an air sample of environmental air in a petroleum refining facility. To illustrate a specific example with reference to FIG. 3, the preventer 460 may comprise the combination of the sample collection enclosure 385, the cup 395, the linear actuator 365, and the microcontroller 360. Whenever the direction detector 430 detects wind is in a first direction, such as blowing in a generally southern direction, the preventer 460 may enable the sample 450 to be exposed to the sample collection device 470.

One skilled in the art of active and passive air sampling and emissions monitoring will appreciate that the sample 450 may not necessarily represent a single sample, or specific fixed volume, of environmental air. Depending on the context, the sample 450 may also refer to a continuous sampling of air. In other words, when the preventer 460 enables the sample 450 to be exposed to the sample collection device 470, the sample 450 may comprise numerous volumes of air samples being exposed to the sample collection device 470.

Continuing with our illustrative example with FIG. 3, the microcontroller 360 may receive a signal indicating the wind flowing in the general southern direction and force the linear actuator 365 to the fully extended position, where the cup 395 is several inches below the sampling ends of the plurality of sample collection devices 380. The microcontroller 360 may receive another signal indicating the wind direction changes and starts flowing in a generally northern direction, whereby the microcontroller 360 may respond by forcing the linear actuator 365 to the fully retracted position and pulling up the cup 395, causing the cup 395 to cover the plurality of sample collection devices 380. As one will appreciate, the pulling the cup 395 up and covering the plurality of sample collection devices 380 may prevent a sample, such as an external air sample, from being collected by the plurality of sample collection devices 380.

Many embodiments of apparatus 410 may also comprise a purger 480. The purger 480 may work in conjunction with the preventer 460 and the direction detector 430 to apply a purge to the sample collection device 470 whenever the preventer 460 operates to prevent the sample collection device from being exposed to the sample 450. Again continuing with our illustrating example using FIG. 3, the purger 480 may comprise the purge gas cylinder 350, the high pressure gauge 345, the pressure regulator 340, the low pressure gauge 330, the rotameter 335, a solenoid valve (not shown), and tubing connecting each of the elements, from the discharge of the purge gas cylinder 350 to the discharge port of the solenoid valve. The discharge tubing from the solenoid valve may be connected to a port of the sample collector enclosure 385. Upon microcontroller 360 receiving a signal that indicates the wind is flowing in a direction in which the environmental air should not be sampled, the microcontroller 360 may respond by forcing the linear actuator 365 to the fully retracted position, closing the cup over the open end of the sample collection enclosure 385, and preventing the plurality of sample collection devices 380 from sampling the air. While the cup 395 is in the fully close position, the microcontroller 360 may also energize the solenoid valve causing purge gas, such as air or nitrogen, to flow from the purge gas cylinder 350 through to the discharge port of the solenoid valve and into the sample collection enclosure 385. In other words, the microcontroller 360 may apply a continuous purge flow to the sample collection enclosure 385 and the plurality of sample collection devices 380 when the plurality of sample collection devices 380 is not sampling the environmental air.

Many embodiments of apparatus 410 may also comprise a data collector 440. For example, in some embodiments the data collector 440 may comprise a small computer or microcontroller coupled with a type of storage medium, such as flash memory or a solid state drive. The data collector 440 may collect operational and environmental data as apparatus 410 operates. Examples of the types of data that the data collector 440 may collect are: air temperature, wind direction (e.g., logged positions of a wind sensor), wind speed, relative humidity, other types of meteorological data, date, time, the operating state of the preventer 460, the number of times the preventer 460 has been activated, the total time or duration that the sample collection 470 device has been in service and/or the amount of time it has been exposed to the environmental air, the amount of time the purger 480 has been in operation, the flowing conditions of the purge gas (flow rate, purge gas cylinder pressure, gas temperature, etc.), the charge state of a battery or condition of the power supply, and any operational errors detected by within the apparatus 410.

One example of a type of error that the data collector 440 may collect is an operational error, such as when a microcontroller in apparatus 410 detects that the wind is flowing in a direction in which the sample 450 should not be collected, that the microcontroller activates the preventer 460, but the preventer 460 fails to operate properly (such as failing to move to the fully closed position). Another type of error that the data collector 440 may collect is a bad power quality condition, such as when the power sags or experiences a voltage spike, or that a solar panel is not properly charging an internal battery. As one skilled in the art will realize, the types of data that the data collector 440 may collect can vary considerably among different embodiments.

One should note that the configuration, number, and type of elements may vary from the embodiment of the apparatus 410 shown in FIG. 4. For example, some embodiments may not comprise any type of data collection device (element 440). Some embodiments may not comprise a means of purging the sample collection device 470. For example, some embodiments may isolate or prevent the sample collection device 470 from not collecting the sample 450, yet not apply any type of purge gas while the sample collection device 470 is prevented from collecting the sample 450.

Additionally, the number, arrangement, and location of elements may vary and not match the arrangement of elements illustrated in FIG. 4. For example, in some embodiments the wind sensor 420 may be a single wind sensor coupled to the enclosure of the apparatus 410. In other embodiments, the wind sensor 420 may comprise a combination of numerous area weather stations that provide indication of wind direction to the direction detector 430 via a wireless communication link.

Figure 5:
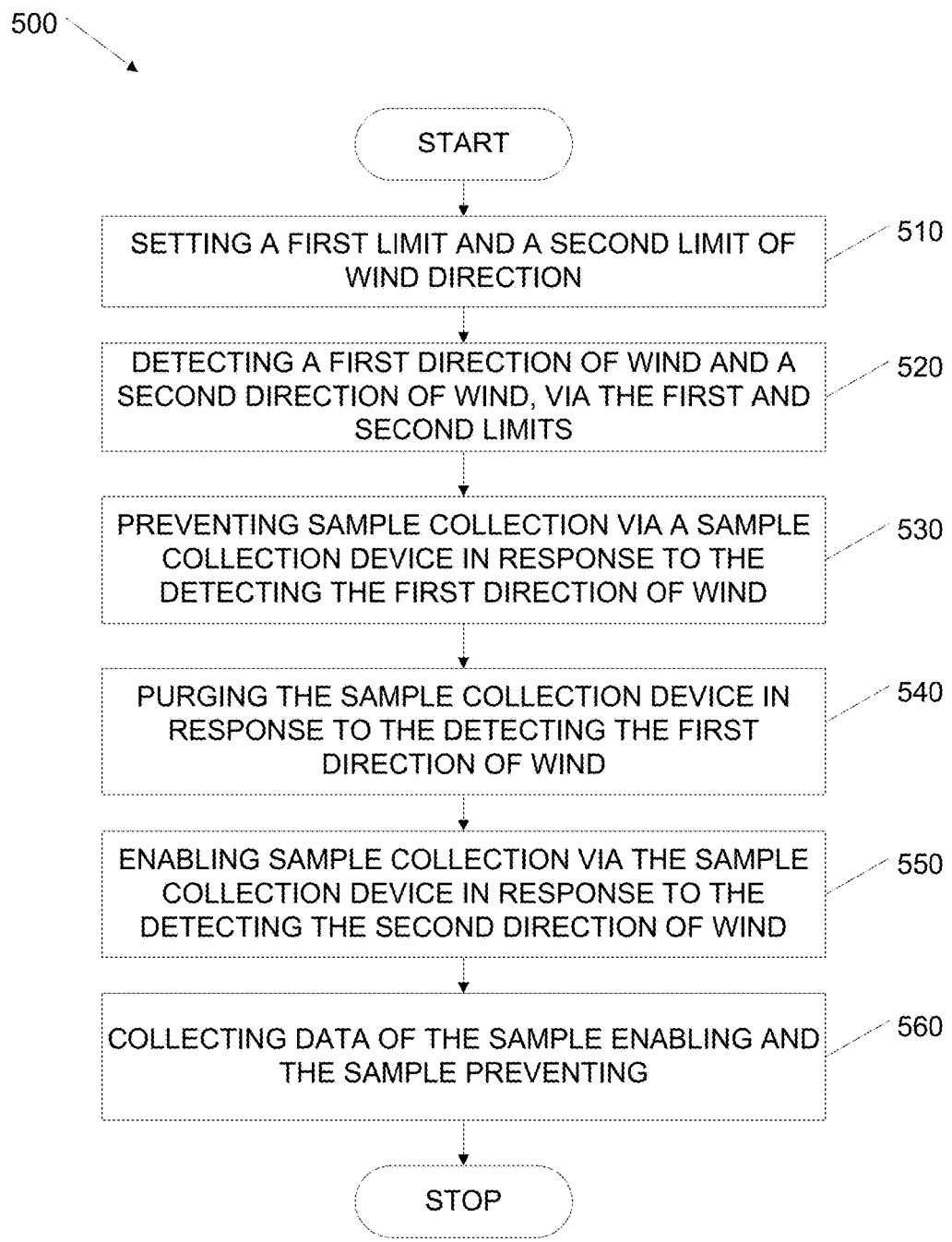
FIG. 5 illustrates a method for air sampling based on wind direction.

FIG. 5 illustrates a method 500 for air sampling based on wind direction. The flowchart for the method 500 begins with setting a first limit and a second limit of wind direction (element 510). For example, an owner of the facility 136 shown in FIG. 1 may wish to set the threshold limits of detection for which the sampling station 164 will enable sample collection. Because the sampling station 164 is located on the northern boundary of the facility 136, the owner may want to set one limit of detection at 0° (degrees), corresponding to direct east, and set a second limit of detection at 180°. The owner may want the sampling station 164 to detect when the wind is blowing out of the north, which would mean the wind is blowing from offsite to onsite. Because air blowing out of the north may contain benzene or some other air toxic from a neighboring facility located to the north of the facility 136, the owner may wish to prevent the sampling station 164 from collecting samples. Consequently, setting the limits of detection at 0° and 180° will enable the sampling station to detect when the wind is blowing out of the north, as will be illustrated in the discussion associated with elements 520, 530, and 550.

An embodiment according to the method 500 may detect a first and a second direction of wind via the limits (element 520). Continuing with our example, if the wind were flowing from offsite to onsite, the sampling station 164 may detect the wind direction is somewhere between the limits of 0° and 180°, such as when the wind vane is pointing to 0.01°, 1°, 5°, 10°, . . . , 175°, 179°, or 179.9999°, as examples. Stated alternatively, the sampling station 164 may detect that the wind direction is at any one of the continually varying points between the limits of 0° and 180°. If the sampling station 164 is coupled to a wind vane that has a sensor that transmits a 0-10 VDC signal as the wind vane travels from 0° to 360°, a wind direction detector unit within the sampling station 164 may detect that the wind is flowing generally from the north by determining the transmitted signal the wind direction detector receives is between 0.0001 VDC (slightly greater than 0 VDC) and 4.9999 VCD (slightly less than 5 VDC).

If the sampling station 164 detects the wind is flowing generally from the north, the sampling station 164 may respond by preventing sample collection (element 530). For example, if the wind direction is flowing from the north to the south (wind vane pointing to 90°, the detector of the sampling station 164 may receive a corresponding 2.5 VDC signal, whereupon the detector will determine that the value of 2.5 VDC corresponds to the wind direction is flowing from direct north (90°) and the sampling station may respond by preventing sample collection. For the sake of illustration, if the sampling station 164 has a sample enclosure like the enclosure depicted in FIG. 2B, the sampling station 164 may prevent sample collection by moving the cup from the open position 285 to the closed position 280. When the cup is in the closed position 280, the sampling station 164 may prevent the diffusive sorbent tube 270 from collecting an air sample.

When the sampling station 164 prevents the diffusive sorbent tube 270 from collecting an air sample, the sampling station 164 may also be configured in a manner that purges the sample collection device (element 540). Continuing again with our example, the sampling station 164 may purge the weather hood 255 with purge gas whenever the cup is in the closed position 280. In some embodiments, the purging may be triggered via a microcontroller. In other embodiments, the purging may be triggered in an alternative manner, such as by a limit switch that activates whenever the cup is in the closed position 280 but deactivates whenever the cup is moved to the open position 285.

As the weather changes, the wind direction may change. If the wind direction changes enough, it may start flowing from a generally southern direction. If the wind starts flowing in a generally southern direction, the air may contain an air toxic that the sampling station 164 needs to collect. Accordingly, the detector may detect that the wind is flowing from a second direction (element 520) by receiving a signal, which may measure between 5.0001 VDC and 10 VDC, from the sensor of the wind vane. In response to the detecting the wind is flowing in the second direction, the sampling station 164 may respond by enabling sample collecting via its sample collection device (element 550). Continuing with our previous example, the direction detector may determine that the wind direction is flowing directly from the south to the north (wind vane pointer at) 270° in response to receiving a 7.5 VDC signal from the sensor of the wind vane. In response, the sampling station 164 may enable sample collection of its diffusive sorbent tube 270 by moving its cup from the closed position 280 to the open position 285.

Many embodiments may also be configured to collect data (element 560). For example, the embodiment may monitor conditions of the wind, environment, and operating status of the sampling station and periodically log or store such information in a manner that may be retrieved. For example, an embodiment may log one or more of the following conditions or parameters, along with a date and timestamp: sampler status (open or closed), wind direction, wind speed, ambient temperature, ambient pressure, relative humidity, battery voltage, and pressure or pressure status of the purge gas.

Those skilled in the art, having the benefit of this disclosure, will appreciate that the embodiments herein contemplate methods, apparatuses, and systems for air sampling and emissions monitoring based on wind direction, including determining concentrations of air toxics. The form of the embodiments shown and described in the detailed description and the drawings are to be taken merely as examples. The following claims are intended to be interpreted broadly to embrace all the variations of the embodiments disclosed.

Although some aspects have been described in detail for some embodiments, it should be understood that various changes, substitutions and alterations can be made herein without departing from the spirit and scope of the embodiments as defined by the appended claims. Although one embodiment may achieve multiple objectives, not every embodiment falling within the scope of the attached claims will achieve every objective. Moreover, the scope of the present specification is not intended to be limited to the particular embodiments of the process, machine, manufacture, composition of matter, means, methods and steps described in the specification. As one of ordinary skill in the art will readily appreciate from the disclosure of the embodiments, processes, machines, manufacture, compositions of matter, means, methods, or steps, presently existing or later to be developed that perform substantially the same function or achieve substantially the same result as the corresponding embodiments described herein may be utilized according to the embodiments herein. Accordingly, the appended claims are intended to include within their scope such processes, machines, manufacture, compositions of matter, means, methods, or steps.

What is claimed is:

1. A method, comprising:
   detecting wind flowing in a first direction;
   exposing a sample collection device to air, wherein the exposing is in response to the detecting wind flowing in the first direction, wherein the exposing the sample collection device comprises exposing a sample collection device comprising a sorbent;
   detecting the wind flowing in a second direction; and
   preventing exposure of the sample collection device to air in response to the detecting the wind flowing in the second direction, wherein the preventing exposure of the sample collection device comprises at least one of closing a sample isolating cup over an open end of an enclosure, wherein the enclosure retains the sample collection device; and
   purging the sample collection device with a purge gas.

2. The method of claim 1, wherein the purging the sample collection device with the purge gas comprises purging the sample collection device with nitrogen.

3. The method of claim 1, wherein the purging the sample collection device with the purge gas comprises purging the sample collection device with purge air from a cylinder.

4. The method of claim 3, wherein the exposing the sample collection device to air comprises enabling the sample collection device to collect an air toxic in the air via adsorption.

5. The method of claim 3, wherein the exposing the sample collection device to air comprises enabling the sample collection device to collect benzene in the air via adsorption.

6. The method of claim 5, wherein the enabling the sample collection device to collect benzene comprises enabling a sorbent tube to collect the benzene via diffusion.

7. An apparatus, comprising:
   a direction detector, wherein the direction detector is configured to receive indication of the direction of wind, wherein the direction detector is configured to detect wind in a first direction via the indication, wherein the direction detector is configured to detect wind in a second direction via the indication;
   an enclosure, wherein the enclosure is configured to retain a sample collection device, wherein the sample collection device comprises a sorbent; and
   a sample preventer, wherein the sample preventer is configured to prevent exposure of the sample collection device to air in response to the direction detector detecting the first direction, wherein the sample preventer is configured to expose the sample collection device to air in response to the direction detector detecting the second direction, wherein the sample preventer is configured to prevent exposure of the sample collection device to air by coupling a sample isolating lid to the enclosure.

8. The apparatus of 7, further comprising a purger, wherein the purger is configured to supply purge gas to the enclosure in response to the direction detector detecting the first direction.

9. The apparatus of claim 8, wherein the enclosure comprises a sample collector enclosure, wherein the preventer is configured to prevent the exposure of the sample collection device to air by coupling the sample isolating lid to the sample collector enclosure.

10. The apparatus of claim 9, wherein the purger comprises a purge gas cylinder, a pressure regulator, and a solenoid valve coupled to the sample collector enclosure.

11. The apparatus of claim 10, wherein the direction detector comprises a microcontroller, wherein the microcontroller is configured to operate the solenoid valve.

12. The apparatus of claim 11, further comprising battery coupled to the microcontroller, further comprising a solar panel coupled to the battery.

13. The apparatus of claim 7, further comprising a wind vane and a sensor coupled to the wind vane, wherein the sensor is configured to provide the indication of the direction of wind.

14. The apparatus of claim 7, wherein the enclosure is configured to retain the sample collection device and a second collection device, wherein at least one of the sample collection device and the second collection device comprises a diffusive sorbent tube.

15. A system, comprising:
a wind indicator, wherein the wind indicator is configured to sense a first direction and a second direction of wind;
a direction detector, wherein the direction detector is configured to receive indication of the first direction and the second direction of wind from the wind indicator; and
a plurality of sampling stations, wherein at least one sampling station of the plurality comprises an enclosure, wherein the enclosure is configured to retain a sample collection device, wherein the at least one sampling station comprises a sample preventer, wherein the sample preventer is configured to prevent exposure of the sample collection device to air via a sample isolating cup in response to the direction detector receiving indication of the first direction of wind, wherein the sample preventer is configured to prevent exposure of the sample collection device to air by coupling the sample isolating cup to the enclosure, wherein the sample preventer is configured to expose the sample collection device to air in response to the direction detector receiving indication of the second direction of wind.

16. The system of claim 15, wherein a second sampling station of the plurality comprises a second enclosure, wherein the second enclosure is configured to retain a second sample collection device, wherein the second sampling station comprises a second sample preventer, wherein the second sample preventer is configured to prevent exposure of the second sample collection device to air in response to the direction detector receiving indication of the second direction of wind, wherein the second sample preventer is configured to expose the second sample collection device to air in response to the direction detector receiving indication of the first direction of wind.

17. The system of claim 16, wherein the sample collection device and the second sample collection device comprise diffusive sorbent tubes.

18. The system of claim 17, further comprising a first purger coupled to the enclosure and a second purger coupled to the second enclosure, wherein the first purger is configured to apply a first purge gas to the sample collection device in response to the direction detector receiving indication of the first direction of wind, wherein the second purger is configured to apply a second purge gas to the second sample collection device in response to the direction detector receiving indication of the second direction of wind.

19. The system of claim 18, further comprising at least one computer, wherein the at least one computer is configured to enable the sample preventer to prevent the exposure of the sample collection device to air, wherein the at least one computer is configured to enable the second sample preventer to prevent the exposure of the second sample collection device to air.

20. The system of claim 16, wherein at least one of the sampling station and the second sampling station comprises a sorbent tube coupled to a pump.

* * * * *